United States Patent [19]

Gristina et al.

[11] Patent Number: 5,585,106
[45] Date of Patent: Dec. 17, 1996

[54] PARTICLE INDUCED AMPLIFICATION OF IMMUNE RESPONSE

[75] Inventors: Anthony G. Gristina, Reston; Girish Giridhar, Manassas Park, both of Va.

[73] Assignee: Medical Sciences Research Institute, Herndon, Va.

[21] Appl. No.: 482,809

[22] Filed: Jun. 7, 1995

Related U.S. Application Data

[60] Continuation-in-part of Ser. No. 197,340, Feb. 16, 1994, which is a division of Ser. No. 885,301, May 18, 1992, Pat. No. 5,292,513.

[51] Int. Cl.⁶ .............................. A61K 9/14; A61F 2/02; A61F 2/28; A61L 9/04
[52] U.S. Cl. .............. 424/401; 424/45; 424/85.1; 424/85.2; 424/426; 424/434; 424/435; 424/445; 424/489; 424/499; 424/501; 514/885; 604/21; 623/16; 623/18
[58] Field of Search ................ 424/45, 85.1, 85.2, 424/401, 426, 434, 435, 489, 499, 501, 445; 514/885; 435/7.24; 436/822; 428/402; 604/21; 623/16, 18

[56] References Cited

U.S. PATENT DOCUMENTS 4,783,484  11/1988  Violanto et al. .................. 514/535
4,826,689   5/1989  Violanto et al. .................. 424/489

*Primary Examiner*—Carlos Azpuru
*Attorney, Agent, or Firm*—Whitham, Curtis, Whitham & McGinn

[57] ABSTRACT

A non-specific host defense cell augmentation technique for enhanced microorganism killing utilizes any phagocytosable particle to prime macrophages for enhanced oxidative response and bacterial killing. The phagocytosable particles should be administered at the time of exposure to contagion, or one day prior to or up to 6–12 hours after exposure. Administration can be performed by any suitable means which will bring the particles quickly into contact with the blood stream where they will encounter phagocytes and cause priming of the patient's macrophages. The augmentation technique provides for non-specific cellular immunity from a wide range of contagion.

14 Claims, No Drawings

PARTICLE INDUCED AMPLIFICATION OF IMMUNE RESPONSE

This invention was made with government support under R01 AR26957 and GM 35939 awarded by the National Institutes of Health. The government has certain rights in this patent.

CROSS-REFERENCE TO RELATED APPLICATIONS

This application is a continuation-in-part application of the application having U.S. Ser. No. 08/197,340 filed Feb. 16, 1994, now allowed, which itself is a divisional of U.S. Ser. No. 07/885,301, filed May 18, 1992, now U.S. Pat. No. 5,292,513, and the complete contents of each of these patent applications and patents are incorporated herein by reference.

DESCRIPTION

DEFINITIONS

1. Phagocyte-a cell that engulfs bacteria and other foreign particles by phagocytosis.
2. Macrophage-a cell derived from the reticuloendothelial system that functions in phagogyctosis. Macrophages are phagocytes.
3. Activate-transforming a cell from a resting state to one where it actively performs its biological function. For example, a macrophage or phagocyte is activated when it encounters a foreign object. Upon encountering the foreign object, the macrophage releases a respiratory burst of oxidizing chemicals to kill or otherwise destroy the object.
4. Elicit-to evoke a response from a cell. For example, foreign objects might, be provided to macrophages to elicit the respiratory burst activity.
5. Priming-converting a cell from resting state to a primed state, whereby, in its primed state, the cell is more active to a biological substance than if the cell had not been primed. For example, an important feature of this invention is that a primed macrophage will have significantly greater oxidative burst activity than a macrophage in its resting state which is activated by a foreign object to elicit the oxidative burst (both will produce an oxidative burst, but the oxidative burst from the primed macrophage is significantly greater).
6. Cytokine-a group of substances formed by an animal in response to infection. Cytokines are similar to hormones in their function, whereby they are produced in one cell and stimulate a response in another cell. Cytokines include such substances as interferon, interleukin, and tumor necrosis factor.

BACKGROUND OF THE INVENTION

1. Field of the Invention

The invention is generally directed to methods and compositions used for protecting a patient (animal or human) from infection. More particularly, the invention is directed to a non-specific host defense augmentation methodology, and compositions useful in the methodology.

2. Description of the Prior Art

Most infections are treated with antibiotics. A distinct disadvantage to antibiotics is that they are often specific for the infecting microorganism. Thus, they cannot provide a patient with protection against the myriad of infection causing agents that may be encountered in, for example, a hospital environment, a natural disaster site, or a military zone. Furthermore, antibiotic compositions are ineffective in foreign-body associated infection, burn infections and infections on contaminated open fractures.

Phagocytes, such as alveolar macrophages, play an important role in controlling microbial infections. Upon encountering a foreign material, such as an invading bacterial cell, phagocytes produce a respiratory burst wherein an oxidative species, such as singlet oxygen, superoxide anion, or hydrogen peroxide. The purpose of the respiratory burst is to produce a battery of oxidizing agents that can be used to destroy the invading microorganism or other foreign material. Many different agents can activate phagocytes to produce an oxidative burst. Thus, the phagocytes provide the animal or human host with a non-specific defense mechanism that can be used to destroy a wide variety of different microorganisms and foreign materials.

It would be advantageous to provide a method and compositions for augmenting a host animal's own non-specific defense mechanism for enhanced activity, thereby providing the patient with superior protection against a wide range of infecting agents.

SUMMARY OF THE INVENTION

It is an object of this invention to provide a method and compositions for augmenting a patient's defense mechanisms to combat infection and a wide variety of infection causing agents.

It is another object of this invention to provide a method of treating patients that have compromised host defense mechanisms, such as patient's with cancer or acquired immunodeficiency syndrome (AIDS).

According to the invention, it has been discovered that the administration of phagocytosable particles to a patient results in a rapid and short term macrophage priming mechanism that can significantly increase (ca. 100-fold increase in lung macrophages) the oxidative response and associated killing capacity of the macrophages. Thus, the phagocytosable particles offer a patient with a non-specific mechanism for controlling and combatting infections under circumstances in which classical cell-mediated immunity does not have time to develop. The host cell augmentation techniqure can be used in a wide variety of applications including the pre-treatment of patients undergoing surgery, the treatment of accident victims suffering from wounds or burns, the treatment of patients with weakened cellular immune systems including those suffering from cancer or acquired immunodeficiency syndrome (AIDS), the prophylactic treatment of personnel being sent to areas with high levels of contagion including war zones and natural disaster sites. In addition, the use of phagocytosable particles offers particular anti-infection benefits to patients receiving implantable biomaterials such as catheters, artificial joints, and bone screws. The particles can be administered by a variety of means that bring the particles into contact with the patient's macrophages, and intravenous injection is preferred. The particles must be of phagocytosable size (0.1–10 µm) and should be administered during the time period of approximately one day prior to exposure to contagion to approximately 6–12 hours after exposure to contagion.

DETAILED DESCRIPTION OF THE PREFERRED EMBODIMENTS OF THE INVENTION

Experiments have been conducted which demonstrate that phagocytosable particles can be effectively used to augment a patient's (animal or human) host defense mechanism to withstand and/or prevent infections. Specifically, the phagocytosable particles cause short term macrophage priming in the patient, whereby the patient's macrophages are primed for a significantly greater oxidative burst upon encountering an infecting organism. The immuno-augmentation methodology is non-specific, thus, it can be used to combat infections stemming from a wide variety of bacteria, viruses, fungi, or other infection causing agents.

Tests show that the patient should be administered the phagocytosable particles on the day of exposure to bacterial infection or one day prior to exposure. Given the rapidity of the macrophage priming effect, phagocytosable particles may be administered up to 12 hours after bacterial or other microorganism exposure to provide the patient with an augmented defensive response.

In practice, the phagocytosable particles could have significant utility in the hospital setting wherein a patient is undergoing elective or required surgery, or is being treated for wounds or burns. In this setting, the patient is exposed to a wide variety of microorganism endemic in hospitals including *Staphylococcus aureus, Pseudomonas aeruginosa, Staphylococcus epidermidis,* and *Streptococcus species (pyogenes)*. These microorganisms give rise to what is clinically referred to as "nosocomial infections". In addition, the patient may be being treated for a wound or burn and has been previously exposed to any of a variety of microbial contaminants. The physician would provide the patient with a sufficient dose of phagocytosable particles to cause macrophage priming in the patient. The dose would be administered shortly before surgery or treatment (approximately one day to a matter of hours), at the time of surgery or treatment, or shortly after surgery or treatment (approximately 6–12 hours after surgery or treatment).

The invention has particular utility in treating or preventing biomaterial based infections. Biomaterials are any material placed inside or on a patient such that the patient's tissues are in contact with the biomaterial. Typical examples include vascular grafts, catheters, artifical joints (hips and knees, etc.), bone fixation rods, plates, screws, allo and autograft tissues, and dressings, etc. It is well understood that biomaterials are a significant source of antibiotic resistant infection causing agents, and that biomaterial focussed infections are a significant problem in the proper treatment of patients.

Biomaterial implants, traumatized tissues and bone are susceptible to immediated and delayed infections because microbes preferentially adhere to "inert biomaterials" or to damaged tissue surfaces. This type of infection is resistant to antibiotic therapy and most often requires removal of the prosthesis or infected tissues.

Microbial adhesion and aggregation, mediated by the glycocalyx "slime" and organized as biofilm, are of intense interest because of their significance in almost all biologic and industrial systems and because of their profound effect on humans in health and disease, especially in biomaterial-centered infections.

Many studies have indicated that once bacteria have developed the biofilm-enclosed, adhesive mode of growth, they become more resistant to biocides, antiseptics, antibiotics, antagonistic environmental factors, and host-defense systems. Free-floating, nonadhesive, or planktonic microbes without an outer layer of exopolysaccharide are more vulnerable to host-clearing mechanisms and are susceptible to lower concentrations of antibacterial agents.

The studies reported in this patent application and the inventor's assessment of the full significance of glycocalyx-mediated adhesive growth on implanted biomaterial suggest two hypotheses: (1) resistant infections are caused by bacterial adhesion to biomaterials with biofilm fromation and (2) the almost impenetrable biofilm explains in part, the resistance of biomaterial-related infectionts to antibiotic therapy and host defenses. Antibiotics, therefore, are most effective prophylactically before biofilm formation.

Tests discussed below indicate that if phagocytosable particles are administered to a patient during the period of 1 day prior to implantation or affixation of the biomaterial to the patient to approximately 6–12 hours post implantation or affixation, infection will be prevented or significantly reduced.

The macrophage priming which results from the administration of phagocytosable particles can have significant advantages in treating patients suffering from cancer. First, it has been established that some tumors are destroyed by activated macrophages, especially sarcomas. The administration of phagocytosable particles will activate the macrophages for enhanced anti-tumor activity. In addition, the enhanced oxidative burst which results from the primed macrophages will increase the reactive oxygen ion species in the vicinity of the tumor which can be used to enhance the effect of radiation on the tumor during therapy. Second, some tumors of lymphoid cell origin cause a marked immunodepression which can result in sever opportunistic infections. Hence, priming the cancer patient's macrophages with phagocytosable particles will provide the patient with antimicrobial activity, thereby preventing these opportunistic infections. Similar advantages can be realized by other patients with immunodepression, such as those suffering from AIDS. AIDS and cancer patients have increased susceptibility to secondary infections; however, their macrophage system is usually preserved until very late stages of the disease. Therefore, the inventive macrophage augmentation effect will be useful in the treatment of such patients for preventing secondary and opportunistic infections. Since the effects of particle administration last only one week or less, the treatment is expected to be non-toxic to tissue cells. The administration can be repeated at periodic times such as monthly or bi-monthly intervals in the treatment of AIDS or cancer patients, or can be provided at the time of radiation therapy in the case of cancer patients.

The particles must be of phagocytosable size or no significant immuno augmentation results. Specifically, it is preferred that the phagocytosable particles be approximately 0.1 to 10 µm. When the particles are 20 µm or greater, the patient's macrophages do not become primed. A wide variety of particulate matter can be used effectively since the response appears to be a biophysical phenomena, that is, the size of the particle appears to be most important parameter for priming the macrophages for enhanced respiratory burst potential (100-fold increase has been observed in alveolar macrophages). The tests discussed below utilized zymosan and latex particles. Zymosan has the advantage of being biodegradable by the body within a matter of days to weeks, whereas latex particles are made of polystyrene and are not generally biodegradable. Thus, biodegradable particles are preferred (but not required) within the practice of this invention. Suitable biodegradable particles include microspheres of L-lactic acid/glycolic acid homo- and co-polymers, gelatin particles, degradable starch complexes, biodegradable hydrogel such as cellulose and poly(2-hydroxyethyl-L-glutamine) (PHEG), hydroxybutyrate and hydroxyvalerate polymers or co-polymers, concanavilin A, colloidal particles of organic origin, degradable polyesters including block co-polymers such as poly(ethylene succinate)-b-poly(ethylene glycol) (PES/PEG), and chitin. If biodegradable particles are used, they should remain relatively intact for 1–4 days to induce the short-term priming of macrophages utilized in the practice of this invention.

Particularly preferred biodegradable particles for immune amplification are poly-D-lactide and liposome particles of size range 10 nanometers to 10 micrometers in diameter. A standard liposome will be prepared with a mixture of commercially available phosphatidylcholine/cholesterol/phosphatidylserine extruded through polycarbonate nucleopore filters. The composition of the particles will be adjusted so that their life span within the phagocytic macrophages is 1–2 weeks. This will be sufficient to cause the required amplification of cellular immunity for the host with no or minimal side effects. It is expected that intracellular phagasome processing of the biodegradables will be complete within one week and that there will be no accumulation of the particle debris in the lymphatics of the reticulo endothelial system.

Additional anti-infection benefits may result if antibiotics, antibodies, or immunoglobulins are associated with the phagocytosable particles.

Administration of the particles can proceed by a wide variety of mechanisms (aerosolized administration to the lungs, etc.), but best results are obtained using intravenous injection. The administration rout should be designed to bring the particles quickly into contact with the blood stream where they will encounter phagocytes and cause priming of the patient's macrophages. If i.v. injection is utilized, the carrier will preferably be an inactive substance such as saline, fats, oils, emulsions, water, and glucose and dextrose solutions. If aerosolized administration is used, the phagocytosable particles should be combined with chlorofluorocarbon, hydrofluorocarbon, or other safe and efficacious propellants (alkanes, dimethyl ether, etc.). Typically, an aerosolized formulation will contain 90% or more propellant.

The optimum dose of the particles can vary depending on the patient and the route of delivery. In short, a sufficient quantity of phagocytosable particles should be supplied to the patient to generate the short term macrophage priming in the patient. Suitable doseages will be approximately 1–10 mg/kg body weight.

The bacteria chosen for the experiments included *S. aureus*, *S. epidermidis*, and *P. auriginosa*. These types of bacteria are the most commonly encountered in treating patients receiving implants (e.g., vascular grafts, catheters, hip and knee joints, bone fixation devices, etc.), and are also the most commonly encountered in patients suffering from wounds (surgical as well as accident victims) and burns. The bacteria are representative of a wide variety of other microorganisms that cause infections in humans and animals including viruses, such as respiratory syncytial virus and entero viruses (polio virus, coxsacki virus); fungi such as candida and aspergillus species; and bacteria such as gram positive *cocci*, *Streptococcus pyogenes*, Pseudomonas species, Hemophilis sp. *enterobactiaceae*, and anaerobic bacteria (bacteroides species). The doses of infective bacteria used in the experiments ($10^{5-8}$ cfu) were deliberately large such that the performance of the immune system augmentation methodology could be tested under severe conditions.

In all cases, the mode of neutralizing the microorganism is to augment the immune system such that the host patient (human or animal) has macrophages that are primed for an enhanced oxidative burst at the time of infection. Thus, the activity is non-specific to the infecting organism.

EXAMPLE 1

Bacterial culture and preparation of inocula

Stock cultures of *S. aureus* ATCC #25923, *S. epidermidis* RP-62A and *P. aeruginosa* IFO 3455 were stored at −70° C. in trypticase soy broth (TSB) supplemented with 30% fetal bovine serum (FBS). Twenty ml of TSB contained in a 125 ml Erlenmyer flask were inoculated with a 100 μl aliquot of stock bacterial culture, and the culture was grown overnight (approximately (ca.) 18 hours) at 37° C. with constant agitation (200 rpm). Two ml of the overnight culture was added to 20 ml of TSB and the new culture was grown for 6 hrs. at 37° C. with agitation. The bacteria contained in 5 ml of the 6-hr-old culture was sedimented by centrifugation (5,000 g, 10 min), were washed once in 20 ml of saline, and were suspended in 5 ml of saline (1X solution). The suspension was serially diluted and 100 μl aliquots were plated on nutrient agar to determine the cfu/ml of the 1X suspension.

Protocol for in vivo amplification of the immune response in rabbits

Adult rabbits (New Zealand White Rabbits, 2–3 kg) were injected intravenously with 20 mg of zymosan (available from Sigma Chemical Co., diameter of approximately 1 μm) or 20 mg of latex (available from Polyscience, Inc., Polybead polystyrene microsphere, 1.03 μm diameter) suspended in 2 ml of sterile saline.

Closed abscess intradermal infection model

Rabbits were anesthetized with ketamine and rompun and an area of about 10 cm×15 cm on the dorsal surface was shaved and depilated. A known number ($10^5$–$10^8$ cfu) of bacteria suspended in 100 μl of saline was injected intradermally with a 26 gauge needle. The formation of lesions was monitored daily for 3 days. The injection sites developed lesions characteristic of the bacterial strain injected. The size of the lesions was recorded on a standard scale of 0 (no lesion, or lesion size less than 5 mm diameter); 1+=5–10 mm diameter lesion; 2+=10–15 mm diameter lesion; 3+=15–20 mm diameter lesion; 4+=20–25 mm diameter lesion; 5+=25–30 mm diameter lesion to 6+=more than 30 mm diameter lesion. The rabbit was sacrificed 2–3 days after bacterial injection, the lesions were excised and cultured on nutrient agar to quantify the remaining bacteria.

RESULTS

Closed abscess intradermal infection model

The intradermal infection model was used for the study because (i) multiple infection sites can be developed on the back of one rabbit, (ii) the inoculation procedure is simple, (iii) the results are reproducible for injection in rabbits, (iv) it readily allows easy evaluation of the severity of infection, and (v) multiple parameters can be investigated on a single animal. The bacteria used in this investigation produced characteristic lesions within one day after intradermal inoculation.

Appearance of lesions from *S. aureus*

*S. aureus* characteristically produced elevated septic lesions in one day after intradermal injection of the bacteria and the lesions grew larger during the three days of experimental period. The lesions developed into closed abscesses with characteristic liquid pus. Inoculation of $10^6$ cfu of the bacteria developed a lesion size of 5+ in three days.

Appearance of lesions from *S. epidermidis* and *P. aeruginosa*

*S. epidermidis* RP-62A and *P. aeruginosa* produced expanded lesions without necrotic core, unlike *S. aureus* which produced elevated lesions. The lesions grew larger during the three days of the experimental period.

Reduction of bacterial (*S. aureus, S. epidermidis,* and *P. aeruginosa*) infection by i.v. administration of zymosan Test rabbits were injected intravenously with zymosan (20 mg/2 ml of saline). After 24 hours, control and test rabbits were intradermally inoculated with various doses ($10^{5-8}$ cfu) of *S. aureus, S. epidermidis* and *P. aeruginosa* (suspended in 100 µl of saline). Sizes of the lesions were measured two days after bacterial challenge on the 0–6+ scale described above which is according to that prescribed in *Materials and Methods*. The results for the *S. aureus, S. epidermidis* and *P. aeruginosa* are presented in Tables 1, 2, and 3, respectively.

TABLE 1

Effect of Zymosan-Induced Immune Amplification on *S. aureus* infection in Rabbit

| | Lesion | |
|---|---|---|
| CFU Injected | Control Rabbit | Primed Rabbit |
| $10^7$ | 4+ | 2+ |
| $10^6$ | 4+ | 0 |
| $10^5$ | 2+ | 0 |

TABLE 2

Effect of Zymosan-Induced Immune Amplification on *S. epidermidis* RP-62A Infection on Rabbit

| | Lesion | |
|---|---|---|
| CFU Injected | Control Rabbit | Primed Rabbit |
| $10^8$ | 3+ | 2+ |
| $10^7$ | 2+ | 1+ |
| $10^6$ | 2+ | 0 |
| $10^5$ | 1+ | 0 |

TABLE 3

Effect of Zymosan-Induced Immune Amplification on *P. aeruginosa* Infection on Rabbit

| | Lesion | |
|---|---|---|
| CFU Injected | Control Rabbit | Primed Rabbit |
| $10^8$ | >6+ | 3+ |
| $10^7$ | 6+ | 3+ |
| $10^6$ | 4+ | 2+ |
| $10^5$ | 3+ | 1+ |

Table 1 shows that when rabbits were intradermally inoculated with infective doses of *S. aureus,* control rabbits developed characteristic elevated septic lesions with liquid pus, whereas zymosan injected rabbits developed comparatively smaller lesions. Cultures of lesions from control rabbits produced numerous colonies; however, cultures of lesions from zymosan injected rabbits were sterile. Table 2 shows that control rabbits infected with *S. epidermidis* produced expanded lesions, whereas zymosan injected rabbits produced comparatively smaller lesions for the same infective doses of bacteria. Table 3 shows that intradermal injection of various infective doses of *P. aeruginosa* produced characteristic lesions on control rabbits. The sites of bacterial inoculation on the back of the rabbits produced dose dependent expanded lesions and signs of cellulitis. However, i.v. administration of zymosan particles one day prior to bacterial challenge significantly reduced the size of lesion, and there was no sign of cellulitis.

Kinetics of particle induced immune amplification effect

Test rabbits were injected intravenously with zymosan particles (20 mg/2 ml saline; c.a. 1 µm) at the time of or 1, 3, or 6 days prior to intradermal challenge with *S. aureus* ($2\times10^6$ cfu). The development of lesions and the effect of zymosan administration on the lesions was monitored. Table 4 shows that rabbits which received zymosan at the time or or one day prior to bacterial challenge developed comparatively smaller lesions, and that injection of zymosan particles more than three days prior to bacterial challenge was less effective in preventing infection.

TABLE 4

Kinetics of Zymosan-Induced Immune Amplification in Preventing *S. aureus* Infection on Rabbits

| Time (days) of Priming Prior to Bacterial Challenge | Lesion |
|---|---|
| No priming (control) | 2+ |
| 0 Time | 0 |
| One Day | 0 |
| Three Days | 1+ |
| Six Days | 1+ |

The results in Table 4 demonstrate that for maximum benefit, the patient should be administered the particles on the day of exposure to bacterial infection or one day prior to exposure. Given the rapidity of the macrophage priming effect, phagocytosable particles may be administered up to 12 hours after bacterial or other microorganism challenge to provide the patient with an augmented defensive response.

Reduction of bacterial infection by i.v. administration of latex particles

Test rabbits were injected intravenously with latex particles (ca. 1 µm diameter; 20 mg/2 ml of saline) one day prior to intradermal inoculation with *S. aureus*. As with the investigations discussed above, the lesions were measured on rated on a 0–6 scale two days after inoculation. Table 5 presents the results.

TABLE 5

Effect of Latex Particle-Induced Immune Amplification on *S. aureus* Infection on Rabbit

| | Lesions | |
|---|---|---|
| CFU Injected | Control Rabbit | Primed Rabbit |
| $2 \times 10^6$ | 5+ | 2+ |
| $2 \times 10^5$ | 3+ | 1+ |

The rabbits injected with latex particles had considerably smaller lesions than those on the control rabbits for the same inoculation dose. Cultures of lesions from the control rabbits showed numerous colonies, whereas cultures of lesions from latex injected rabbits had significantly fewer colonies.

Post Challenge Immune Amplification for Preventing Bacterial Infection

As discussed above, rabbits were anesthetized and areas of about 10 cm×15 cm on the back were shaved and depilated. A known cfu of bacteria (*S. aureus* ATCC#25293) was injected intradermally to elicit infections. One day after the bacterial challenge, test animals were injected intravenously with latex beads (ca. 1 µm in diameter). The development of lesions and the effect of immune amplification by the latex injection was recorded for four days. The size of the lesions was recorded using the 0–6+ rating system described above.

Table 6 shows that the size of the lesions on control rabbits and particle treated rabbits were similar for the same infective doses of bacteria. Thus, particle induced immune amplification one day after bacterial challenge did not significantly reduce the severity of bacterial infection, although marginal protection against infection was noticed. In view of these results, treatment at the time of bacterial challenge or one day prior to challenge is optimum. It is expected that treatment just after bacterial challenge (e.g., 6–12 hours) will also yield satisfactory results.

TABLE 6

Post-Challenge Immune Amplification in Preventing Infection

| Treatment | CFU | Lesion size after days | | | |
|---|---|---|---|---|---|
| | | 1 | 2 | 3 | 4 |
| Experiment 1 | | | | | |
| control | $10^6$ | 2+ | 3+ | — | 3+ |
| control | $5 \times 10^5$ | 1+ | 2+ | — | 2+ |
| primed | $10^6$ | 2+ | 2+ | — | 2+ |
| primed | $5 \times 10^5$ | 1+ | 1+ | — | 1+ |
| Experiment 2 | | | | | |
| control | $10^6$ | 1+ | — | 2+ | 3+ |
| control | $5 \times 10^5$ | 0 | — | 1+ | 1+ |
| primed | $10^6$ | 1+ | — | 2+ | 3+ |
| primed | $5 \times 10^5$ | 0 | — | 1+ | 1+ |

EXAMPLE 2

Biomaterial-associated resistant bacterial infections are serious complications of implant surgery. Opportunistic pathogens adhere to and colonize biomaterial surfaces and are resistant to antibiotics and host defenses. It has been reported that interaction of macrophages with biomaterials over time results in the reduced bactericidal function of macrophages, thus increasing susceptibility to bacterial infections. The short-term immuno augmentation technique of this invention, which utilizes phagocytosable particles to prime macrophages for an enhanced respiratory burst, can be used successfully to reduce biomaterial-associated bacterial infections.

Materials and Methods

Preparation of Bacterial Inocula

Stock culture of S. aureus ATCC #25923 was maintained in TSB supplemented with 30% FBS under 70° C. Twenty ml of TSB contained in 125 ml of Erlenmyer flask was inoculated with 100 µl of stock bacterial culture and the culture was grown overnight (ca. 18 hrs) at 37° C. with constant agitation at 200 rpm. The bacteria contained in 2 ml of overnight culture was added to fresh 20 ml of PBS and the new culture was grown for 7 hrs at 37° C. with constant agitation. The bacteria contained in 5 ml of the 7 hr culture were sedimented by centrifugation at 5,000 g for 10 min. The bacteria were washed once with 20 ml of saline and were suspended in 5 ml of saline (1× suspension). The cfu/ml of 1× suspension was determined by serial dilution and colony counts on nutrient agar.

Protocol for In Vivo Immune Amplification of Rabbits

Test rabbits were injected intravenously with 20 mg of zymosan (approximately 1 µm in diameter, antigenic) or 20 mg of latex particles (ca. 1 µm diameter, non-antigenic) suspended in 2 ml saline one day prior to bacterial challenge.

Closed Abscess Foreign Body Intradermal Infection Model

Rabbits were anesthetized and an area of about 10 cm×15 cm was shaved and depilated. A known number (1–5×$10^4$ cfu) of S. aureus suspended in 100 µl saline was administered intradermally with a 26 gauge needle. Selected sites received bacteria together with 0.5 mg/per site of polymethylmethacrylate (PMMA) beads (0.3 µm). The injection sites developed lesions characteristic of the type of bacteria injected. The size of the lesions were recorded daily using the 0 to 6+ scale described above. The rabbits were sacrificed 2–3 days after bacterial injection and the lesions excised. The excised lesions were cultured on nutrient agar to quantify the remaining viable bacteria.

Results

Intradermal inoculation of S. aureus caused characteristic elevated lesions one day after bacterial inoculation. The lesions formed closed abscesses with characteristic liquid pus. The size of the lesions was dose dependent. In the presence of PMMA beads, the lesions were clearly more severe and expanded. On the contrary, intravenous administration of zymosan (antigenic) or latex (non-antigenic) particles prior to bacterial challenge considerably reduced the severity of wound and PMMA-associated infection. Cultures of lesions of the sites (with or without PMMA) from control rabbits showed numerous bacterial colonies, whereas cultures of sites from immune amplified rabbits (those receiving particles) showed fewer colonies.

EXAMPLE 3

Similar experiments to that described in Example 2 were conducted to demonstrate that the particulate priming of macrophages to protect against infection was applicable to different strains of bacteria (e.g., the non-specific nature of the host defense system), and was useful in the presence of biomaterials such as PMMA beads, and wire materials (stainless steel and titanium wire). Similar materials and methods, amplification procedures, and infection models to those described in Examples 1 and 2 were used.

a. Latex-Particle-Induced Immune Amplification to Prevent or Reduce PMMA-Beads-Associated S. Aureus Infection.

Materials and Methods-Test rabbits were injected with 20 mg of latex particles (1.03 µm diameter) in 2 ml of saline. After 24 hrs., S. aureus ($10^{5-6}$ CFU) were injected intradermally to elicit infection. Companion sites received bacteria plus PMMA beads (0.3 µm diameter; 0.5 mg per site). The sizes of the lesions and the effect of immune amplification on the prevention of infection were recorded 3 days post-infection. Results-Lesions were formed based on the infective doses of bacteria injected. Table 7 shows that the presence of PMMA beads considerably enhanced the severity of infection, and that immune amplification with latex beads prevented or greatly reduced the severity of infection (Table 7 is the average of 3 experiments).

TABLE 7

| CFU Injected | Type of Rabbits | Sizes of Lesions | |
|---|---|---|---|
| | | Without PMMA | With PMMA |
| $10^6$ | Control | 3.3 ± 1 | 4.6 ± 1.4 |
| | Primed | 1.5 ± 0.5 | 2.3 ± 0.5 |
| $10^5$ | Control | 2.5 ± 0.5 | 5.0 ± 1 |
| | Primed | 0 | 1.5 ± 0.5 | b. Prevention Staphylococcus epidermidis RP 62A Foreign Body (Biomaterial) Centered Infection by Latex-Induced Immune Amplification Materials and Methods-Test rabbit was immune amplified by intravenous injection of latex particles (20 mg/2 ml of saline, c.a. 1 µm diameter). After 24 hrs, the immune amplified rabbit and one control rabbit were anesthetized and areas of about 10 cm×15 cm on the back were shaved and depilated. Two sites were injected intradermally with $7×10^6$ CFU of *S. epidermidis* RP 62A and two other sites with $7×10^5$ CFU of *S. epidermidis*. Companion sites were injected with the same doses of bacteria plus a foreign body in the form of polymethylmethacrylate (PMMA) (an example of cement used for total joint fixation) at 5 mg of 0.3 μm diameter beads per bacterial injection site. The development of lesions and effect of immune amplification by latex injection were recorded for five days. The sizes of the lesions were recorded on the same scale as described above.

Results-Table 8 shows *S. epidermidis* by itself failed to cause infection in the intradermal region of the rabbits. Addition of the foreign body (PMMA beads) along with bacteria caused infection; lesion size 2+ for $7×10^6$ cfu of bacteria and lesion size 1+ for $7×10^5$ cfu of bacteria. Immune amplification considerably reduced the severity of infection or totally prevented infection.

TABLE 8

| CFU Injected | With or Without PMMA | Lesion Size | |
|---|---|---|---|
| | | Control Rabbit | Primed Rabbit |
| $7 × 10^6$ | Without PMMA | 0 | 0 |
| | With PMMA | 2+ | 1+ |
| $7 × 10^5$ | Without PMMA | 0 | 0 |
| | With PMMA | 1+ | 0 |

This is a significant experiment which duplicates actual clinical conditions wherein *S. epidermidis* usually will not infect unless there is a foreign body (biomaterial) present. *S. epidermidis* is now responsible for approximately 50% of prosthetic implant infections (total joints, vascular grafts, contact lenses, etc.).

c. Latex-Induced Immune Amplification to Prevent Titanium or Stainless Steel Wire Associated *S. aureus* Infection Materials and Methods-Test Rabbits were primed by intravenous injection of latex beads 1.09 μm diameter; 20 mg/2 ml saline) one day prior to bacterial challenge.

Titanium wire (Ti; 0.81 mm×10 mm) and surgical grade stainless steel K wire (SS; 0.8 mm×10 mm) were sterilized. To attach bacteria, the wires were incubated with $10^8$ CFU of *S. aureus* for 1 hr at 37° C. with constant agitation (100 rpm). The wires were then washed to remove unattached bacteria. To determine the number of bacteria attached to the wire, contaminated sample wires were sonicated in 1 ml sterile saline using water-bath sonicator for 10 min to release the bacteria attached to the wire into the saline. The bacterial suspensions were serially diluted, plated on nutrient agar and incubated at 37° C. for 24 hrs. The colony developed were counted.

Two sterile and two contaminated Ti and SS wires were inserted into the intradermal region of rabbits. The infections and effect of priming in prevention infection were recorded for five days.

Results-Approximately $3×10^5$ cfu of bacteri attached per Ti wire, whereas approximately $3×10^4$ cfu of bacteri attached per SS wire. Table 9 shows that there was no infection after five days on sites implanted with sterile wires. Large infection was noticed on sites implanted with contaminated wire. Prophylactic immune amplification prevented or considerably reduced the severity of injection, thus indicating the particle-induced immune amplification can be successfully used to prevent or greatly reduce the severity of injection associated with metallic and other solid implants.

TABLE 9

| Status of Rabbits | Size of Lesions | |
|---|---|---|
| | Titanium | Stainless Steel |
| Control | 7+, expanded with pus | — |
| Primed | 3+, confined with pus | — |
| Control | 5+, with pus | 3+, with pus |
| Primed | 1+, no pus | 0, no lesion |

Although the chronic presence of large numbers of non-biodegradable particulates generates destructive inflammation, the short term presence of phagocytosable biodegradable bacteria and zymosan, and some non-biodegradable particulates (latex particles) is the first step in the up regulation of non-specific cell mediated immunity for enhanced microbicidal effects. Significantly, in studying these responses, the inventors have discovered that the intratracheal (i.t.) (aerosol) or intravenous (i.v.) administration of both non-antigenic and antigenic particulates rapidly (1–3 days) upregulates or primes macrophages for a 100X enhanced oxidative response when subsequently elicited by phagocytized bacteria. The priming is non-specific, occurs rapidly and declines by 1 week post injection, thus indicating that specific antigen expanded T cell clonal and memory based immunity are not involved.

Recent publications have provided crucial insights in our knowledge oft cell and NK cell maturation pathways for the production of Mφ priming/activation factor(s), and directly support the hypothesis that the initial phagocytosis of particulates results in the production of IL-12 and TNFα which direct the maturation of naive T cells to $T_H1$ cells and the production of interferon-gamma ($IFN_\gamma$) by $T_H1$ cells and NK cells. The IL-12, $IFN_\gamma$ circuit is rapid, occurring within three days. It has been demonstrated that IL-12 produced by Listeria infected Mφ stimulated $IFN_\gamma$ production and induced differentiation of $T_H1$ cells from uncommitted (naive) T cells at 2–4 days, which resulted in the initiation of cell mediated immunity. Heat-killed *L. monocytogenes* and severely combined immunodeficiency (SCID) spleen cells have been used in vitro to show that IL12 and TNFα are co-stimulators of NK cell-$IFN_\gamma$ production, to show that IL-2 maximizes the $IFN_\gamma$ response, and to show that IL-10 inhibits production of IL-12, TNF, and $IFN_\gamma$. Studies have also shown that $IFN_\gamma$, TNF, lipopolysaccharide (LPS), microbes, and non-antigenic particles trigger or elicit reactive oxygen ions (ROI), nitric oxide, and cytokine activation.

Based on the data discussed above and the litierations, it is suggested that initial exposure of Mφ to microbes, microbial products, or particulates is a designed and conserved evolutionary signal for the release of IL-12 and TNFα, the subsequent maturation of $T_H1$ cells, the production of $IFN_\gamma$ and NK cells, and the recruitment and priming for enhanced activation of additional Mφ for an enhanced oxidative burst which provides resistance to infection in the short term (1–2 weeks) while clonal specific memory based immunity is induced inf the particles are antigenic. The initial phagocytosing Mφ expend themselves on the first bacteria or particulates, and release ROI, nitric oxide, and IL-12 as a signal for $T_H1$ maturation, $IFN_\gamma$ production, and additional primed Mφ for an enhanced oxidative burst when challenged by bacteria. Significantly, the results above demonstrate that animals are protected from a lethal challenge of *P. aeruginosa* and to *S. aureus* infection using the particle immunoaugmentation model.

While the invention has been described in terms of its preferred embodiments, those skilled in the art will recognize that the invention can be practiced with modification within the spirit and scope of the appended claims.

We claim:

1. A method of preventing microbial infections via non-specific immunity, comprising the step of:

administering to a patient in need thereof a sufficient quantity of phagocytosable particles of a size ranging from 0.01 to 10 μm to prime macrophages in said patient for enhanced macrophage activity, said step of administering being performed during a time period ranging from approximately one day prior to exposure to microbial agents to approximately 6–12 hours after exposure to said microbial agents, said phagocytosable particles lacking biocides and pharmaceuticals and consisting of materials selected from the group consisting of phosphatidylcholine, cholesterol, or phosphatidylserine and mixtures thereof, polylactide L-lactic acid/glycolic acid homopolymers, L-lactic acid/glycolic acid copolymers, gelatin particles, degradable starch complexes, hydrogels, hydroxybutyrate/hydroxyvalerate co-polymers, polyesters, chitin, cellulose, opsonized zymosan, polymethylmethacrylate, latex, polystyrene, and mixtures thereof.

2. The method of claim 1 wherein said step of administering is performed at approximately the same time as exposure to said microbial agents.

3. The method of claim 1 wherein said step of administering is performed at approximately one day prior to exposure to said microbial agents.

4. The method of claim 1 wherein said step of administering is performed intravenously.

5. The method of claim 1 wherein said phagocytosable particles are biodegradable.

6. The method of claim 1 wherein said phagocytosable particles are liposomes formed from phosphatidylcholine, cholesterol, or phosphatidylserine or mixtures thereof.

7. The method of claim 1 further comprising the step of implanting or affixing a biomaterial to said patient.

8. The method of claim 7 wherein said biomaterial is selected from the group consisting of catheters, bone screws, artificial joints, bandages, and dressings.

9. A composition for enhancing non-specific cellular immunity, comprising:

a pharmaceutically acceptable carrier fluid;

an effective dose of a plurality of phagocytosable particles, said phagocytosable particles lacking biocides and pharmaceuticals and consisting of materials selected from the group consisting of phosphatidylcholine, cholesterol, or phosphatidylserine and mixtures thereof, polylactide, L-lactic acid/glycolic acid homopolymers, L-lactic acid/glycolic acid copolymers, gelatin particles, degradable starch complexes, hydrogels, hydroxybutyrate/hydroxyvalerate co-polymers, polyesters, chitin, cellulose, opsonized zymosan, polymethylmethacrylate, latex, polystyrene, and mixtures thereof, said phagocytosable particles having a diameter ranging from 0.01 to 10 μm dispersed in said pharmaceutically acceptable carrier fluid, and wherein said effective dosage is between 0.01 mg and 10 mg per kg of body weight of those in need of enhancing non-specific cellular immunity.

10. The composition of claim 9 wherein said carrier fluid is an injectable liquid.

11. The composition of claim 9 wherein said particles are non-biodegradable.

12. The composition of claim 9 wherein said particles consists of latex particles.

13. The composition of claim 9 wherein said particles are selected from the group consisting of liposomes, polylactide particles, and biodegradable particles.

14. The composition of claim 9 wherein said particles consists of liposomes.

\* \* \* \* \*